United States Patent [19]

Share

[11] Patent Number: 5,466,721
[45] Date of Patent: Nov. 14, 1995

[54] CITRAL ACETAL ETHERS OF ALPHA-HYDROXY PHENYL KETONES AND RADIATION CURABLE COMPOSITIONS THEREOF

[75] Inventor: Paul E. Share, Berwyn, Pa.

[73] Assignee: Henkel Corporation, Plymouth Meeting, Pa.

[21] Appl. No.: 258,917

[22] Filed: Jun. 13, 1994

Related U.S. Application Data

[63] Continuation of Ser. No. 73,007, Jun. 4, 1993, abandoned.

[51] Int. Cl.$^6$ .............................. C08F 2/50; C08G 59/17; C07C 49/255
[52] U.S. Cl. .................... 522/34; 522/103; 522/904; 526/316; 568/329; 568/330; 568/331; 568/336
[58] Field of Search ............................... 522/34; 568/329, 568/330, 331, 336

[56] References Cited

U.S. PATENT DOCUMENTS

| Re. 29,131 | 2/1993 | Smith et al. | 260/77.5 |
|---|---|---|---|
| 3,935,330 | 1/1976 | Smith et al. | 427/41 |
| 4,144,156 | 3/1979 | Kuesters | 522/34 |
| 4,190,602 | 2/1980 | Brunisholz | 522/34 |
| 4,308,400 | 12/1981 | Felder | 568/336 |
| 4,469,774 | 9/1984 | Lee | 430/270 |
| 4,477,326 | 10/1984 | Lin | 522/34 |

OTHER PUBLICATIONS

Y. Kurusu et al., "The Synthesis and Reaction of the Polymer Bearing Benzoin and Furoin Structure", *Die Makromolekulare Chemie*, vol. 138, pp. 49–58 (1970).

J. Lowell, "Coating Methods", *Enclyclopedia of Polymer Science and Engineering*, vol. 3, pp. 615–675, 552–671, and supp. vol., pp. 53, 109, 110; and Acrylamide Polmer, vol. 1, pp. 234–299 and 169–211.

E. J. Murphy et al., "Some Charactaeristics of Steric Polymerization," *Proceedings of RadTech 1990—North America*, vol. 1, pp. 217–226.

*Primary Examiner*—Mark A. Chapman
*Attorney, Agent, or Firm*—Ernest G. Szoke; Wayne C. Jaeschke; John Daniel Wood

[57] ABSTRACT

Provided are compounds having the formula:

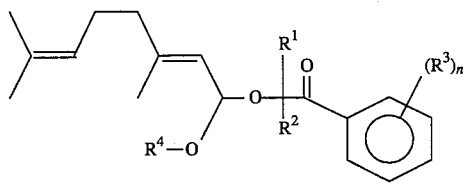

wherein:
$R^1$ and $R^2$ are independently selected from the group consisting of a hydrogen atom, an aliphatic group, a hetero-aliphatic group, an aromatic group, and a heterocyclic group, provided that $R^1$ and $R^2$ may together form a divalent radical selected from the group consisting of an aliphatic radical and hetero-aliphatic group;
each $R^3$ is independently selected from the group consisting of an aliphatic group, a hetero-aliphatic group, an aromatic group, and a heterocyclic group;
$R^4$ is selected from the group consisting of an aliphatic group, a hetero-aliphatic group, an aromatic group, and a heterocyclic group; and
n is an integer from 0 to 5.

Also provided are polymerizable compositions containing such compounds and a method of coating a substrate which uses such polymerizable compositions.

68 Claims, No Drawings

CITRAL ACETAL ETHERS OF ALPHA-HYDROXY PHENYL KETONES AND RADIATION CURABLE COMPOSITIONS THEREOF

This application is a continuation of application Ser. No. 08/073,007 filed on Jun. 4, 1993 now abandoned.

FIELD OF THE INVENTION

The present invention relates to polymerizable compounds, to radiation curable compositions and to radiation curable coatings. More particularly, it relates to a process for preparing coatings which employs a single compound as both a monomer and a photoinitiator.

BACKGROUND ART

The polymerization of acrylate esters in general to form polymers is well known. Certain acrylate and/or vinyl polymers containing a benzoin functional group are known. U.S. Pat. No. 4,469,774 discloses positive-working photosensitive benzoin esters used in contact litho films, lithographic and relief printing plates and photoresists. The polymers are prepared by polymerizing an acrylate or methacrylate ester of an alkoxybenzoin compound. The use of acrylate monomers may be restricted in the future by governmental regulations relating to the environment, and thus, alternatives to acrylate monomers are of practical interest.

Y. Kurusu et al., "The Synthesis and Reaction of the Polymer Bearing Benzoin and Furoin Structure", *Die Makromolekulare Chemie*, Vol. 138, pp. 49–58 (1970) discloses the preparation of a polymers containing a benzoin structure. In one preparation, a polystyrene polymer is treated with phenyl glyoxal to obtain the polymer poly-4'-vinylbenzoin. In another preparation, a copolymer of styrene and maleic anhydride is reacted with benzoin in such a manner that the anhydride group of the maleic anhydride unit esterifies the hydroxyl group of the benzoin molecule. These polymers are described as being photo-sensitive such that the polymer will crosslink upon exposure to radiation.

The technology for the production of coatings by curing monomeric compositions in general on the surface of various substrates is known. For example, J. Lowell, "Coatings", *Encyclopedia of Polymer Science and Engineering*, vol. 3, pp. 615–675, discusses, at page 647, the production of coatings by free-radical polymerization of monomers, e.g unsaturated polyesters in a solution of an unsaturated monomer such as styrene, acrylates, and methacrylates, and polyfunctional low volatility monomers such as trimethylolpropane triacrylate. When such systems are cured with ultra-violet radiation, a photoinitiator such as benzophenone is often used to increase the production of free-radicals and thereby promote curing of the coating.

SUMMARY OF THE INVENTION

The present invention relates to compounds of the formula I:

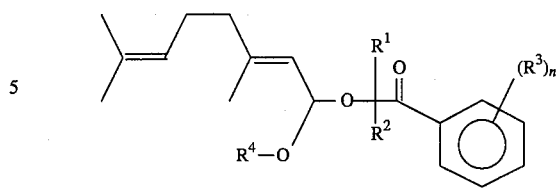

wherein:

$R^1$ and $R^2$ are independently selected from the group consisting of a hydrogen atom, an aliphatic group, a hetero-aliphatic group, an aromatic group, and a heterocyclic group (preferably from the group consisting of a hydrogen atom, an alkyl group, a substituted alkyl group, an aromatic group, and a substituted aromatic group and preferably provided that at least one of $R^1$ and $R^2$ is a group other than a hydrogen atom), provided that $R^1$ and $R^2$ may together form a divalent radical selected from the group consisting of an aliphatic radical and hetero-aliphatic group (preferably a straight-chain pentylene radical);

each $R^3$ is independently selected from the group consisting of an aliphatic group, a hetero-aliphatic group, an aromatic group, and a heterocyclic group, (preferably from the group consisting of lower alkyl groups and lower alkoxy groups);

$R^4$ is selected from the group consisting of an aliphatic group, a hetero-aliphatic group, an aromatic group, and a heterocyclic group, (preferably from the group consisting of lower alkyl groups); and n is an integer from 0 to 5.

The compounds described above are both polymerizable and capable of initiating free-radical polymerization. Thus, the compound can act as a self-initiating monomer, i.e. it can act as the photoinitiator for its own polymerization (homopolymerization or copolymerization) or can act as a secondary curing agent (e.g. when homopolymerized or copolymerized by non-photochemical techniques and then cured upon exposure to radiation). An advantage of this self-initiation aspect lies the reduction in extractables from the composition upon curing, i.e. because the photoinitiator is reacting into the polymer, there should be little or no photoinitiator susceptible to extraction from the cured polymer. This reduction of extractibles is desirable from the standpoint of possible environmental concerns about the possibility of leaching of compounds from the polymer into the environment.

In preferred compounds, $R^2$ is selected from the group consisting of hydrogen and lower alkyl, each $R^3$ is selected form the group consisting of hydrogen, lower alkyl, and lower alkoxy, $R^4$ is lower alkyl and n is 0. In a preferred class of compounds $R^1$ is has the formula:

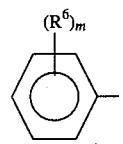

wherein each $R^6$ is selected from the group consisting of an aliphatic group, a hetero-aliphatic group, an aromatic group, and a heterocyclic group, (preferably from the group consisting of lower alkyl groups) and m is an integer from 0 to 5. In another preferred class of compounds, $R^1$ and $R^2$ are both methyl groups or together form a straight-chain divalent pentylene radical (i.e.—$(CH_2)_5$—), This invention also relates to a polymerizable composition comprising a polymerizable benzocarbonyl-functional citral acetal compound of formula I. Said composition is preferably essentially free of other compounds susceptible to initiation of free-radical polymerization of said composition upon exposure to ultra-violet radiation. In certain embodiments, the composition will further comprise a second polymerizable compound, e.g. a mono-olefinically substituted, said second copolymerizable compound optionally being present in a major amount by weight of the composition. In another aspect of the invention, the composition will further comprise a thermal initiator to allow the composition to be first cured by thermal means and then secondarily cured by exposure to radiation.

This invention also relates to a method of forming a polymer in contact with a substrate comprising (i) contacting a surface of a substrate with a composition comprising a benzocarbonyl-functional citral acetal compound of formula I, and (ii) exposing said surface to radiation sufficient to cause said benzocarbonyl-functional acetal of citral to polymerize on said surface. In preferred embodiments of this method, the composition further comprises a first polymerizable monomer and a minor amount of said benzocarbonyl-functional acetal of citral. The method may be practiced in the context of forming a protective and/or decorative coating on the substrate, adhering the substrate to a second surface, sealing voids in the substrate and/or between the substrate and a second article, and/or casting or molding of the polymerizable composition to form an article.

DETAILED DESCRIPTION OF THE INVENTION

The compounds of this invention are defined by the formula above. The terms used to describe the various groups are intended to have their ordinary meanings, unless otherwise noted. Aliphatic radicals include any (a) straight chain and branched alkyl radicals having from 1 to about 50 carbon atoms; (b) cycloalkyl radicals having from 4 to about 20 carbon atoms; (c) straight chain and branched alkenyl radicals having from 2 to about 40 carbon atoms; (d) cycloalkenyl radicals having from 5 to about 20 carbon atoms; (e) straight chain and branched alkynyl radicals having from 2 to about 30 carbon atoms; cycloalkenyl radicals having from 6 to about 20 carbon atoms. Aliphatic radicals also include those above-mentioned aliphatic radicals which contain one or more heteroatoms substituted for one or more hydrogen or carbon atoms. The heteroatoms include the halogens, nitrogen, sulfur, oxygen, and phosphorus or groups of heteroatoms such as nitro, sulfonic acid, $C_{1-10}$ alkyl sulfonate ester, sulfoxide, sulfone, phosphoryl, trihalomethyl.

An aromatic radical is any benzenoid or non-benzenoid aromatic radical having from 4 to 50 carbon atoms. A non-benzenoid aromatic radical excludes simple phenyl groups, but includes polynuclear aromatic, other carbocyclic aromatic radicals (e.g. those having cycloaliphatic groups), and heterocyclic aromatic radicals. For purposes of this invention, a substituted aromatic radical is any benzenoid or non-benzenoid aromatic radical having from 4 to 50 carbon atoms wherein one or more hydrogen atoms is replaced by an atom or a group of atoms other than hydrogen including the alkyl, alkenyl, alkoxy, halogens, nitrogen, sulfur, oxygen, and phosphorus or groups of heteroatoms such as nitro, sulfonic acid, $C_{1-10}$ alkyl sulfonate ester, sulfoxide, sulfone, phosphoryl, trihalomethyl, and the like. Such an aromatic radical also includes those radicals which contain other aliphatic moieties, aromatic groups, and/or hetero atoms.

The compounds of this invention can be made by a variety of different reaction schemes, but a particularly useful scheme is as follows:

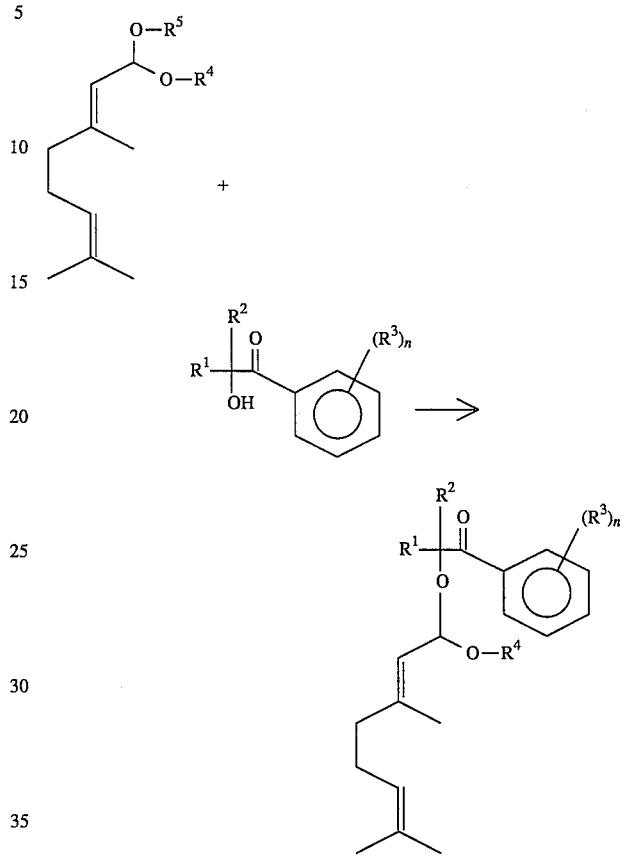

wherein the variables are as set forth above and $R^5$ is a monovalent radical which facilitates formation of the leaving $R^5$—OH. $R^5$ is preferably a lower alkyl group (i.e. $C_1$ to $C_4$ alkyl, e.g. methyl). The above reaction can be characterized as a transacetalization of a citral acetal with a benzocarbonyl-functional alcohol. The citral acetal starting material is commercially available and is readily prepared from citral and, for example, lower alkanols by conventional means. The benzocarbonyl-functional alcohol is commercially available or can be readily prepared by conventional means. For example, in the preferred compound wherein $R^1$ is an unsubstituted phenyl group, the starting benzocarbonyl-functional compound employed in the reaction set forth above is benzoin, a material that is readily available commercially. When $R^1$ and $R^2$ are methyl, the benzocarbonyl-functional compound is alpha-hydroxy-alpha,alpha-dimethyl-acetophenone which is commercially available as Darocure 1173 and when $R^1$ and $R^2$ together form a straight-chain pentylene radical, the compound is 1-benzoylcyclohexanol which is commercially available as Irgacure 184.

The choice of reaction conditions in the above reaction is important due to the acid-sensitivity of the citral acetal starting material. This starting material readily decomposes in the presence of acids at even moderately high temperatures. Because the transacetalization is acid catalyzed, the reaction medium should be maintained at a relatively low temperature. However, volatilization of the $R^5$—OH alcohol formed as a by-product of the reaction is a means of driving the reaction to substantial completion. To drive the reaction to completion, but maintain a moderate temperature in the reaction medium, it is preferred that vacuum distillation be employed to remove the by-product alcohol. It is also preferred that $R^5$ is a lower alkyl group so that the resulting alcohol volatilizes at low temperatures with only moderately reduced pressures.

Other components that may be useful in the polymerizable compositions of this invention are any materials which are capable of addition copolymerization with the benzocarbonyl-functional citral acetal compounds of formula I described above to form a useful polymer composition. The polymerizable components include mono-ethylenically unsaturated monomers capable of homopolymerization, or copolymerization with other ethylenically unsaturated monomers, as well as copolymerization with the benzocarbonyl-functional citral acetal compound. Examples of suitable mono-ethylenically unsaturated compounds include alkyl acrylates (e.g. lower alkyl acrylates), alkyl methacrylates, acrylamides (e.g. lower N-alkyl acrylamides), vinyl esters, vinyl amines and vinyl aromatic compounds. The polymerization of acrylate monomers is discussed in *Encyclopedia of Polymer Science and Engineering*, vol. 1, pp. 234–299 (John Wiley & Sons, Inc., N.Y., N.Y., 1985) and the polymerization of acrylamide monomers is discussed in *Encyclopedia of Polymer Science and Engineering*, vol. 1, pp. 169–211 (John Wiley & Sons, Inc., N.Y., N.Y., 1985), the disclosure of which is incorporated by reference. Specific examples of polymerizable compounds include acrylic acid, methacrylic acid, butyl acrylate, methoxyethyl acrylate, butyl methacrylate, ethyl acrylate, t-butyl acrylate, 2-ethylhexyl acrylate, methyl methacrylate, lauryl methacrylate, vinyl acetate, N-vinyl pyrrolidinone, styrene, and vinyl toluene, acrylamide, N,N-dimethylacrylamide, N,N-diethylacrylamide, N-acryloyl-morpholine, N-acryloyl-piperidine, acrylic acid anilide, methacrylic acid anilide, maleic anhydride, maleates, itaconates, styrene, vinyltoluene, chlorostyrene, methoxystyrene, chloromethylstyrene, 1-vinyl-2-methylimidazole, 1-vinyl-2-undecylimidazole, 1-vinyl-2-undecylimidazoline, N-vinylpyrrolidone, N-vinylcarbazole, vinylbenzyl ether, and vinylphenyl ether.

The polymerizable composition may be comprised of a crosslinking compound. Such a compound will have the activity of increasing the degree of hardening or the viscosity of the cured polymerizable composition. Such crosslinking compounds are so-called poly-functional monomers having a plurality of ethylenic or vinyl groups or vinylidene groups in the molecule. The amount of the crosslinking compound will vary depending upon the contemplated application of the cured polymeric composition, but will generally be sufficient to cure the composition upon exposure to ultra-violet radiation. The degree of cure of the composition can be determined by conventional techniques, e.g., resistance to solvents (e.g., swelling, extractibles, and/or spot-testing). In preferred compositions, the amount of crosslinking compound will be sufficient to measurably increase the gel content of the cured polymeric composition, e.g., preferably by at least about 1% and more preferably at least about 5%. Typical levels of crosslinking compound will range from about 0. 1 to about 25% by weight of the polymerizable components of the polymerizable composition.

Examples of a number of the poly-functional monomers include methylene-bis-acrylamide, trimethylene-bis-acrylamide, hexamethylene-bis-acrylamide, N,N'-diacryloylpiperazine, m-phenylene-bis-acrylamide, p-phenylene-bis-acrylamide, ethylene glycol diacrylate, propylene glycol dimethacrylate, diethylene glycol diacrylate, polyethylene glycol diacrylate, bis(4-acryloxypolyethoxyphenyl)propane, 1,5-pentanediol diacrylate, neopentyl glycol diacrylate, 1,6-hexanediol acrylate, polypropylene glycol diacrylate, pentaerythritol triacrylate, trimethylolpropane triacrylate, pentaerythritol tetraacrylate, N-methylol-acrylamide, diacetone-acrylamide, triethylene glycol dimethacrylate, pentaerythritol tetra-allyl ether.

Polymerizable materials that may also be included in the polymerizable composition include and oligomers and polymers. Examples of useful reactive oligomers include low molecular weight polymers (e.g., about 1,000 to 25,000 g/mole) having polymerizable ethylenic unsaturation. Specific examples include maleic-fumaric unsaturated polyesters, acrylate-terminated polyesters (e.g. those described in U.S. Pat. No. Re 29,131 to Smith et al.) acrylic copolymers having pendant vinyl unsaturation (e.g. allyl acrylate/acrylic copolymers), epoxy acrylates (e.g. Photomer 3015, available from Henkel Corporation, Ambler, Pa.), and polyurethane acrylates (e.g. Photomer 6210, available from Henkel Corporation, Ambler, Pa.). Examples of useful reactive polymers include graft polymerizable polyolefins, e.g., polyethylene, polypropylene, and ethylene/propylene copolymers, and polymers having polymerizable ethylenic unsaturation along the backbone, for example diene homopolymers or copolymers (e.g., styrene-butadiene copolymers, cis-polybutadiene, and butadiene-acrylonitrile copolymers).

The polymerizable component and benzocarbonyl-functional citral acetal compound can be mixed in any convenient manner which will place the component and compound in a sufficiently reactive association to form a polymer on subsequent curing thereof. Generally, simple mixing of the polymerizable component and benzocarbonyl-functional citral acetal compound will suffice. Other useful techniques include conventional wet chemistry techniques, e.g., dissolution in a common solvent system.

The amount of the benzocarbonyl-functional citral acetal compound will vary depending upon the contemplated application of the cured polymeric composition, but will generally be sufficient to initiate polymerization of the composition upon exposure to ultra-violet radiation. This polymerization will be the initial polymerization of the benzocarbonyl-functional citral acetal compound or a secondary curing of the polymer containing a polymeric unit derived from the benzocarbonyl-functional citral acetal compound. The degree of polymerization of the composition can be determined by conventional techniques, e.g. viscosity (particularly in the case of initial polymerization) or resistance to solvents (particularly in the case of secondary curing of a polymerized and post-cured composition).

In typical applications, the amount of the benzocarbonyl-functional citral acetal compound in the polymerizable composition will range from about 0.1% to about 25% by weight of the composition. However, it may be desirable in some applications to use the benzocarbonyl-functional citral acetal compound in a major amount by weight of the polymerizable composition (e.g. as the sole polymerizable monomer). Typically, however, the amount of the benzocarbonyl-functional citral acetal compound in the polymerizable composition will be minor. An upper limit on the amount for a given application is functionally determined for a given polymerizable composition by the absorbance of polymerizing radiation by the benzocarbonyl-functional citral acetal compound and the masking effect that results if excessive levels of the compound are employed.

For example, if a coating containing the benzocarbonyl-functional citral acetal compound is exposed to radiation and the level of the compound employed is sufficient to cause that portion of the polymerizable composition that is closest to the radiation source to absorb essentially all of the radiation, then that portion of the polymerizable composition that is away from the radiation source, e.g. that portion closest to the substrate, will not be polymerized. Thus, the benzocarbonyl-functional citral acetal compound should not be employed at levels in a coating which will prevent the exposure of all of the composition to sufficient radiation to polymerize the composition to the degree desired. (Of course, if the coating is of a sufficiently small thickness in relation to the intensity of the radiation, or if incomplete photo-cure is desired, e.g a post-thermal cure is desired, then this masking effect will not be of concern.) A practical lower limit on the amount of the benzocarbonyl-functional citral acetal compound will be determined by the degree of photoinitiation and/or secondary curing that is needed or desired for a given polymerizable composition. Typical levels of benzocarbonyl-functional citral acetal compound, i.e. when the primary use is as an initiator that exhibits minimal extractability from the polymerized composition (e.g. when it is desired that the compound as a monomeric unit have a minimal effect on the physical properties of the resulting polymer) will range from about 0.01% to about 5% by weight of the polymerizable components of the polymerizable composition, preferably from about 0.1% to about 2%.

The polymerizable composition of the present invention can be applied to a variety of substrates. These include, for example, porous stock such as paper and cardboard, wood and wood products, metals such as aluminum, copper, steel, and plastics such as P.V.C., polycarbonates, acrylics and the like. The compositions are applied by methods such as spraying, rollcoating, flexo and gravure processes onto a selected substrate. The resulting coated substrate, e.g., a paper, is typically cured under UV or electron beam radiation. The compositions may optionally include other substances such as pigments, resins, monomers and additives such as antioxidants and rheological modifiers. Methods of coating and materials used in coatings are described in *Encyclopedia of Polymer Science and Engineering*, vol. 3, pp. 552–671 and supp. vol., pp. 53, 109 and 110 (John Wiley & Sons, Inc., N.Y., N.Y., 1985), the disclosure of which is incorporated by reference.

The coated surface is then exposed to sufficient radiation to cure the reactive diluent through the radiation sensitive pi bonds. Suitable sources of radiation include ultraviolet light, electron beam or radioactive sources such as are described in U.S. Pat. No. 3,935,330 issued Jan. 27, 1976 to Smith et al. To enhance the rate of radiation curing of the composition, an accelerator may be added to the composition. Examples of accelerators include mercaptans, e.g. pentaerythritol tetramercaptopropionate. (One advantage of the use of the benzocarbonyl-functional citral acetal compounds of this invention is that the citral moiety tends to mask, or render less unpleasant, the objectionable odor of a mercaptan accelerator.)

The composition may, however, be essentially free of conventional photoinitiators, i.e. other benzocarbonyl-functional compounds e.g. benzoin, benzoin ethers, 1-benzoylcyclohexanol, alpha-hydroxy-alpha,alpha-dimethylacetophenone. The composition may contain thermal initiators such as organic peroxides, hydroperoxides, peroxy acids, peroxy esters, azo compounds, ditertiary butyl peroxide, benzoyl peroxide, 2,4-dichlorobenzoyl peroxide, tertiary butyl hydroperoxide, 1,5-dimethyl-2,5-bis(hydroperoxy)hexane, peroxyacetic acid, peroxybenzoic acid, tertiary butyl peroxypivalate, tertiary butyl peroxyacetic acid and azobisisobutyronitrile. The addition of a thermal initiator will allow the initial polymerization of the benzocarbonyl-functional citral acetal compound into a polymer followed by post-cure of the polymer upon exposure to ultra-violet radiation.

To ensure that the composition does not prematurely polymerize, a free radical inhibitor may be added to the polymerizable composition. Examples of suitable inhibitors include hydroquinone and the methyl ether thereof or butylated hydroxy toluene at a level of from about 5 ppm to about 2000 ppm by weight of the polymerizable components.

The amount of radiation necessary to cure the composition will of course depend on the angle of exposure to the radiation, the thickness of the coating to be applied, and the amount of polymerizable groups in the coating composition, as well as the presence or absence of a free radical initiating catalyst. For any given composition, experimentation to determine the amount of radiation sensitive pi bonds not cured following exposure to the radiation source is the best method of determining the amount and duration of the radiation required. Typically, an ultra-violet source with a wavelength between 200 nm and 300 nm (e.g. a filtered mercury arc lamp) is directed at coated surfaces carried on a conveyor system which provides a rate of passage past the ultra-violet source appropriate for the radiation absorption profile of the composition (which profile is influenced by the degree of cure desired, the thickness of the coating to be cured, and the rate of polymerization of the composition).

The polymerizable compositions of this invention may also find use as a starting material for applications in addition to coatings. Particular examples include articles formed by the shaping (e.g. casting, molding, or extrusion) of polymeric materials, as well as binders (e.g. for pigments of printing inks, magnetic media, etc.), or by use of the composition as an adhesive or sealant. Further, steric polymerization techniques as described by E. J. Murphy et al., "Some Characteristics of Steric Polymerization", *Proceedings of RadTech 1990—North America*, vol. I, pp. 217–226, the disclosure of which is incorporated herein by reference, may be useful. In such techniques, where a pool of polymerizable composition is subjected to a focused laser beam of ultra-violet radiation, an object is formed within the pool from discrete thin layers formed at the top of the pool where the laser beam is focused. In a sense, the composition polymerizes in contact with the surface of a layer of cured polymer.

The particular procedures used in a given application of the polymerizable composition and the choice of the other necessary or desirable starting materials, catalysts, and other functional additives, as well as the amount of benzocarbonyl-functional citral acetal compound, will be within the skill of the art within which the polymerizable composition is employed.

The following examples will serve to further illustrate the invention, but should not be construed to limit the invention, unless expressly set forth in the appended claims. All parts, percentages, and ratios are by weight unless otherwise indicated in context.

EXAMPLES

Coating Procedures and Apparatus

In the following examples, coatings were prepared by the following procedure. The substrates used, unless noted otherwise, were aluminum panels available commercially as Q-panels from Q-Panel Corporation, and are coated using RDS Coating Rods. The curing apparatus was a Fusion Systems Model F440 with a 300 watt/inch mercury bulb. The variables in the tests include the speed of the belt which transports the substrate under the bulb, the number of passes the substrate makes under the bulb, and the thickness of the coating on the substrate, and variations in the coating formulation, e.g. type and amount of additives and co-monomers, which will be noted below.

Example 1

This example illustrates a procedure for the synthesis of benzoin methyl citral acetal. Into a 3-necked, 1 liter round bottomed flask fitted with a magnetic stirrer, reflux condenser, thermometer with a temperature regulator, heating mantle, and a vacuum source, were charged 297.50 grams citral dimethyl acetal and 212.50 grams benzoin. The mixture was stirred and heated to 80 degrees C., with a concomitant lowering of the pressure to maintain a controlled evolution of volatile components. Once the desired temperature was achieved, the heating source was removed, and the reaction mixture was allowed to cool to 60 degrees C.

Nitrogen gas was then added to the evacuated vessel to raise the pressure to atmospheric. Under a flow of nitrogen was added dropwise a solution of 300 milligrams p-toluenesulfonic acid in 5 ml acetonitrile. The pressure in the reaction vessel was then lowered to allow the evolution of volatiles, and heating was resumed to obtained a regulated temperature of 90 degrees C. The heating was maintained for a period of 24 hours, during which time the pressure in the reaction vessel was gradually decreased in order to keep the liquid at its boiling point.

After 24 hours, the reaction mixture was a homogeneous clear liquid, and was allowed to cool to 50 degrees C. before pouring into a pint sample bottle under nitrogen at atmospheric pressure. Small amounts of unreacted benzoin which precipitated from the liquid during the first several days of shelf storage were separated from the reaction product by filtration.

Example 2 and Comparative Examples 3 and 4

Coating formulations were prepared using a benzoin citral acetal compound prepared by the same, or substantially similar procedures, as in Example 1 above. This coating was prepared by mixing 4 parts by weight of the neat benzoin methyl citral acetal was mixed with 96 parts by weight of an epoxy acrylate monomer available from Henkel Corporation, Ambler, Pa. as Photomer 3015. This formulation was coated at a thickness 6.86 micrometers and was then cured in a single pass at the belt speed set forth in Table 1, below. Comparative formulations were prepared by substituting 4 parts by weight of the commercial photoinitiator Irgacure 1173 or Irgacure 651 (Comparative Examples 3 and 4, respectively) for the benzoin methyl citral acetal.

TABLE 1

| Ex. | Belt Speed (ft/min) | Pencil Hardness | Adhesion | MEK Rubs |
|---|---|---|---|---|
| 2 | 100 | 4H | 0 | 22 |
| 2 | 100 | 4H | 0 | 27 |
| 2 | 100 | 4H | 0 | 26 |
| 2 | 300 | 2B | 0 | 5 |
| 2 | 300 | 2B | 0 | 7 |
| 2 | 300 | 2B | 0 | 15 |
| 2 | 500 | 4B | 0 | 3 |
| 2 | 500 | 4B | 0 | 4 |
| 2 | 500 | 4B | 0 | 3 |

TABLE 1-continued

| Ex. | Belt Speed (ft/min) | Pencil Hardness | Adhesion | MEK Rubs |
|---|---|---|---|---|
| 3 | 100 | 3H | 0 | 88 |
| 3 | 100 | 3H | 0 | 17 |
| 3 | 100 | 3H | 0 | 26 |
| 3 | 300 | 3H | 0 | 16 |
| 3 | 300 | 3H | 0 | 51 |
| 3 | 300 | 3H | 0 | 23 |
| 3 | 500 | 2H | 0 | 12 |
| 3 | 500 | 2H | 0 | 31 |
| 3 | 500 | 2H | 0 | 19 |
| 4 | 100 | 5H | 0 | 100 |
| 4 | 100 | 5H | 0 | 100 |
| 4 | 100 | 5H | 0 | 100 |
| 4 | 300 | 4H | 0 | 100 |
| 4 | 300 | 4H | 0 | 85 |
| 4 | 300 | 4H | 0 | 90 |
| 4 | 500 | 4H | 0 | 76 |
| 4 | 500 | 4H | 0 | 56 |
| 4 | 500 | 4H | 0 | 55 |

Example 5 and Comparative Examples 6 and 7

Coating formulations were prepared using a benzoin citral acetal compound prepared by the same, or substantially similar procedures, as in Example 1 above. This coating was prepared by mixing 4 parts by weight of the neat benzoin methyl citral acetal was mixed with 96 parts by weight of a urethane acrylate monomer available from Henkel Corporation, Ambler, Pa., as Photomer 6210. This formulation was coated at a thickness 6.86 micrometers and was then cured in a single pass at the belt speed set forth in Table 2, below. Comparative formulations were prepared by substituting 4 parts by weight of the commercial photoinitiator Irgacure 1173 or Irgacure 651 (Comparative Examples 6 and 7, respectively) for the benzoin methyl citral acetal.

TABLE 2

| Ex. | Belt Speed (ft/min) | Pencil Hardness | Adhesion | MEK Rubs |
|---|---|---|---|---|
| 5 | 100 | 2H | 0 | 3 |
| 55 | 100 | 2H | 0 | 3 |
| 5 | 100 | 2H | 0 | 4 |
| 5 | 300 | 1H | 0 | 3 |
| 5 | 300 | 1H | 0 | 3 |
| 5 | 300 | 1H | 0 | 3 |
| 5 | 500 | 1B | 0 | 2 |
| 5 | 500 | 1B | 0 | 2 |
| 5 | 500 | 1B | 0 | 2 |
| 6 | 100 | 5H | 0 | 8 |
| 6 | 100 | 5H | 0 | 8 |
| 6 | 100 | 5H | 0 | 7 |
| 6 | 300 | 4H | 0 | 6 |
| 6 | 300 | 4H | 0 | 6 |
| 6 | 300 | 4H | 0 | 14 |
| 6 | 500 | 4H | 0 | 6 |
| 6 | 500 | 4H | 0 | 6 |
| 6 | 500 | 4H | 0 | 6 |
| 7 | 100 | 5H | 0 | 4 |
| 7 | 100 | 5H | 0 | 7 |
| 7 | 100 | 5H | 0 | 6 |
| 7 | 300 | 5H | 0 | 3 |
| 7 | 300 | 5H | 0 | 3 |
| 7 | 300 | 5H | 0 | 3 |
| 7 | 500 | 5H | 0 | 5 |
| 7 | 500 | 5H | 0 | 6 |
| 7 | 500 | 5H | 0 | 5 |

Example 8 and Comparative Example 9

Coating formulations were prepared using a benzoin citral acetal compound prepared by the same, or substantially similar procedures, as in Example 1 above. This coating was prepared by mixing 4 parts by weight of the neat benzoin methyl citral acetal was mixed with 96 parts by weight of an epoxy acrylate monomer available from Henkel Corporation, Ambler, Pa. as Photomer 3015. This formulation was coated at a thickness 6.86 micrometers on aluminum and was then cured in a single pass at a belt speed of 100 ft./min. Comparative formulations were prepared by substituting 4 parts by weight of the commercial photoinitiator Irgacure 651 (Comparative Example 9) for the benzoin methyl citral acetal.

The films were collected from their respective panels and each were placed in separate vessels, each vessel containing identical amounts of tetrahydrofuran. The vessels were shaken for one hour, stored overnight, reshaken for one hour and the supernatant solution from each was analyzed by gas chromatography for the presence of Irgacure 651 and the benzoin methyl citral acetal compound, respectively. Analysis of the extract from the film cured with Irgacure 651 indicated that all 4 parts (100% within the limits of detection) of the Irgacure 651 added to the coating formulation was extracted into the solvent. Analysis of the extract of the film cured with the benzoin methyl citral acetal compound indicated that 2.5 parts by weight of the original 4 parts (62.5%) were extracted into the solvent.

What is claimed is:

1. A compound of the formula:

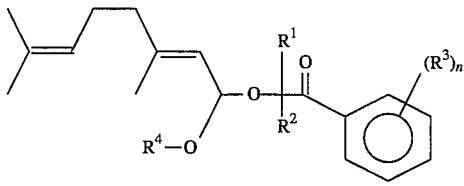

wherein:
- $R^1$ and $R^2$ are independently selected from the group consisting of a hydrogen atom, an aliphatic group, a hetero-aliphatic group, an aromatic group, and a heterocyclic group, provided that $R^1$ and $R^2$ may together form a divalent radical selected from the group consisting of an aliphatic radical and hetero-aliphatic group;
- each $R^3$ is independently selected from the group consisting of an aliphatic group, a hetero-aliphatic group, an aromatic group, and a heterocyclic group;
- $R^4$ is selected from the group consisting of an aliphatic group, a hetero-aliphatic group, an aromatic group, and a heterocyclic group; and
- n is an integer from 0 to 5.

2. A compound of claim 1 wherein $R^1$ and $R^2$ are selected from the group consisting of a hydrogen atom, an alkyl group, a substituted alkyl group, an aromatic group, and a substituted aromatic group provided that one of $R^1$ and $R^2$ is a group other than a hydrogen atom.

3. A compound of claim 1 wherein $R^2$ is hydrogen or lower alkyl.

4. A compound of claim 1 wherein each $R^3$ is independently selected from the group consisting of lower alkyl groups and lower alkoxy groups.

5. A compound of claim 1 wherein n is 0.

6. A compound of claim 1 wherein $R^4$ is selected from the group consisting of lower alkyl groups.

7. A compound of claim 1 wherein $R^1$ is phenyl, lower alkylphenyl or lower alkoxyphenyl.

8. A compound of claim 1 wherein $R^1$ is a phenyl group.

9. A compound of claim 1 wherein $R^1$ has the formula:

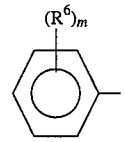

wherein $R^6$ is selected from the group consisting of an aliphatic group, a hetero-aliphatic group, an aromatic group, and a heterocyclic group, and m is an integer from 0 to 5.

10. A compound of claim 9 wherein $R^6$ is selected from the group consisting of lower alkyl and lower alkoxy.

11. A compound of claim 9 wherein m and n are 0.

12. A compound of claim 9 wherein each $R^3$ is independently selected from the group consisting of lower alkyl groups and lower alkoxy groups, n is 0, 1, or 2, and $R^4$ is selected from the group consisting of lower alkyl groups.

13. A compound of claim 12 wherein $R^1$ is phenyl, lower alkylphenyl or lower alkoxyphenyl, m is 0, 1 or 2, and $R^2$ is hydrogen or lower alkyl.

14. A compound of claim 13 wherein m and n are 0.

15. A compound of claim 13 wherein $R^2$ is hydrogen, and $R^4$ is methyl.

16. A compound of claim 12 wherein $R^1$ and $R^2$ are methyl groups or together form a divalent radical selected from the group consisting of an aliphatic radical and hetero-aliphatic radical.

17. A compound of claim 16 wherein $R^1$ and $R^2$ are both methyl or together form a straight-chain pentylene radical.

18. A compound of claim 1 wherein $R^1$ is phenyl, lower alkyl, or together with $R^2$ forms a straight-chain pentylene radical, $R^2$ is hydrogen, lower alkyl or together with $R^1$ forms a straight-chain pentylene radical; $R^4$ is lower alkyl.

19. A compound of claim 18 wherein $R^4$ is methyl.

20. A compound of claim 1 wherein $R^1$ is phenyl, $R^2$ is hydrogen, n is zero, and $R^4$ is methyl.

21. A compound of claim 1 wherein $R^1$ is methyl, $R^2$ is methyl, n is zero, and $R^4$ is methyl.

22. A compound of claim 1 wherein $R^1$ together with $R^2$ forms a straight-chain pentylene radical, n is zero, and $R^4$ is methyl.

23. A polymerizable composition comprising a polymerizable benzocarbonyl-functional citral acetal compound having the formula:

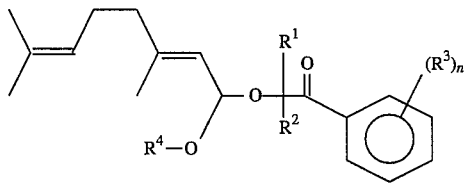

wherein:
- $R^1$ and $R^2$ are independently selected from the group consisting of a hydrogen atom, an aliphatic group, a hetero-aliphatic group, an aromatic group, and a heterocyclic group, provided that $R^1$ and $R^2$ may together form a divalent radical selected from the group consisting of an aliphatic radical and hetero-aliphatic group;
- each $R^3$ is independently selected from the group consisting of an aliphatic group, a hetero-aliphatic group, an aromatic group, and a heterocyclic group;

R⁴ is selected from the group consisting of an aliphatic group, a hetero-aliphatic group, an aromatic group, and a heterocyclic group; and n is an integer from 0 to 5.

24. A polymerizable composition of claim 23 wherein R¹ and R² are selected from the group consisting of a hydrogen atom, an alkyl group, a substituted alkyl group, an aromatic group, and a substituted aromatic group provided that one of R¹ and R² is a group other than a hydrogen atom.

25. A polymerizable composition of claim 23 wherein R² is hydrogen or lower alkyl.

26. A polymerizable composition of claim 23 wherein each R³ is independently selected from the group consisting of lower alkyl groups and lower alkoxy groups.

27. A polymerizable composition of claim 23 wherein n is 0.

28. A polymerizable composition of claim 23 wherein R⁴ is selected from the group consisting of lower alkyl groups.

29. A polymerizable composition of claim 23 wherein R¹ is phenyl, lower alkylphenyl or lower alkoxyphenyl.

30. A polymerizable composition of claim 23 wherein R¹ is a phenyl group.

31. A polymerizable composition of claim 23 wherein R¹ has the formula:

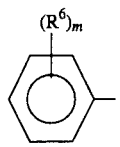

wherein R⁶ is selected from the group consisting of an aliphatic group, a hetero-aliphatic group, an aromatic group, and a heterocyclic group and m is an integer from 0 to 5.

32. A polymerizable composition of claim 31 wherein R⁶ is selected from the group consisting of lower alkyl and lower alkoxy.

33. A polymerizable composition of claim 31 wherein m and n are 0.

34. A polymerizable composition of claim 31 wherein each R³ is independently selected from the group consisting of lower alkyl groups and lower alkoxy groups, n is 0, 1, or 2, and R⁴ is selected from the group consisting of lower alkyl groups.

35. A polymerizable composition of claim 34 wherein R¹ is phenyl, lower alkylphenyl or lower alkoxyphenyl, m is 0, 1 or 2, and R² is hydrogen or lower alkyl.

36. A polymerizable composition of claim 35 wherein m and n are 0.

37. A polymerizable composition of claim 35 wherein R² is hydrogen, and R⁴ is methyl.

38. A polymerizable composition of claim 34 wherein R¹ and R² are methyl groups or together form a divalent radical selected from the group consisting of an aliphatic radical and hetero-aliphatic radical.

39. A polymerizable composition of claim 38 wherein R¹ and R² are both methyl or together form a straight-chain pentylene radical.

40. A polymerizable composition of claim 23 wherein R¹ is phenyl, lower alkyl, or together with R² forms a straight-chain pentylene radical, R² is hydrogen, lower alkyl or together with R¹ forms a straight-chain pentylene radical; R⁴ is lower alkyl.

41. A polymerizable composition of claim 40 wherein R⁴ is methyl.

42. A polymerizable composition of claim 23 wherein R¹ is phenyl, R² is hydrogen, n is zero, and R⁴ is methyl.

43. A polymerizable composition of claim 23 wherein R¹ is methyl, R² is methyl, n is zero, and R⁴ is methyl.

44. A polymerizable composition of claim 23 wherein R¹ together with R² forms a straight-chain pentylene radical, n is zero, and R⁴ is methyl.

45. A polymerizable composition of claim 23 wherein said composition is essentially free of other compounds susceptible to initiation of free-radical polymerization of said composition upon exposure of said composition to ultraviolet radiation.

46. A method of polymerizing a composition in contact with a substrate comprising:

contacting a surface of a substrate with a composition comprising a benzocarbonyl-functional citral acetal compound having the formula I:

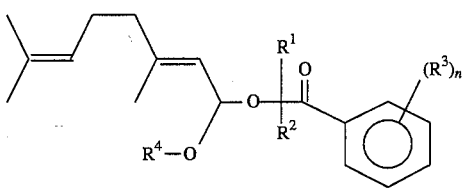

wherein:

R¹ and R² are independently selected from the group consisting of a hydrogen atom, an aliphatic group, a hetero-aliphatic group, an aromatic group, and a heterocyclic group, provided that R¹ and R² may together form a divalent radical selected from the group consisting of an aliphatic radical and hetero-aliphatic group;

each R³ is independently selected from the group consisting of an aliphatic group, a hetero-aliphatic group, an aromatic group, and a heterocyclic group;

R⁴ is selected from the group consisting of an aliphatic group, a hetero-aliphatic group, an aromatic group, and a heterocyclic group; and n is an integer from 0 to 5; and exposing said surface to radiation sufficient to cause said benzocarbonyl-functional acetal of citral to polymerize on said surface.

47. A method of claim 46 wherein R¹ and R² are selected from the group consisting of a hydrogen atom, an alkyl group, a substituted alkyl group, an aromatic group, and a substituted aromatic group provided that one of R¹ and R² is a group other than a hydrogen atom.

48. A method of claim 46 wherein R² is hydrogen or lower alkyl.

49. A method of claim 46 wherein each R³ is independently selected from the group consisting of lower alkyl groups and lower alkoxy groups.

50. A method of claim 46 wherein n is 0.

51. A method of claim 46 wherein R⁴ is selected from the group consisting of lower alkyl groups.

52. A method of claim 46 wherein R¹ is phenyl, lower alkylphenyl or lower alkoxyphenyl.

53. A method of claim 46 wherein R¹ is a phenyl group.

54. A method of claim 46 wherein R¹ has the formula:

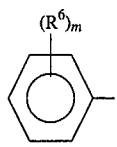

wherein $R^6$ is selected from the group consisting of an aliphatic group, a hetero-aliphatic group, an aromatic group, and a heterocyclic group and m is an integer from 0 to 5.

55. A method of claim 54 wherein $R^6$ is selected from the group consisting of lower alkyl and lower alkoxy.

56. A method of claim 54 wherein m and n are 0.

57. A method of claim 46 wherein each $R^3$ is independently selected from the group consisting of lower alkyl groups and lower alkoxy groups, n is 0, 1, or 2, and $R^4$ is selected from the group consisting of lower alkyl groups.

58. A method of claim 57 wherein $R^1$ is phenyl, lower alkylphenyl or lower alkoxyphenyl, m is 0, 1 or 2, and $R^2$ is hydrogen or lower alkyl.

59. A method of claim 58 wherein m and n are 0.

60. A method of claim 58 wherein $R^2$ is hydrogen, and $R^4$ is methyl.

61. A method of claim 57 wherein $R^1$ and $R^2$ are methyl groups or together form a divalent radical selected from the group consisting of an aliphatic radical and hetero-aliphatic radical.

62. A method of claim 61 wherein $R^1$ and $R^2$ are both methyl or together form a straight-chain pentylene radical.

63. A method of claim 46 wherein $R^1$ is phenyl, lower alkyl, or together with $R^2$ forms a straight-chain pentylene radical, $R^2$ is hydrogen, lower alkyl or together with $R^1$ forms a straight-chain pentylene radical; $R^4$ is lower alkyl.

64. A method of claim 63 wherein $R^4$ is methyl.

65. A method of claim 46 wherein $R^1$ is phenyl, $R^2$ is hydrogen, n is zero, and $R^4$ is methyl.

66. A method of claim 46 wherein $R^1$ is methyl, $R^2$ is methyl, n is zero, and $R^4$ is methyl.

67. A method of claim 46 wherein $R^1$ together with $R^2$ forms a straight-chain pentylene radical, n is zero, and $R^4$ is methyl.

68. A method of claim 46 wherein said composition is essentially free of other compounds susceptible to initiation of free-radical polymerization of said composition upon exposure of said composition to ultra-violet radiation.

* * * * *

UNITED STATES PATENT AND TRADEMARK OFFICE
CERTIFICATE OF CORRECTION

PATENT NO.  : 5,466,721
DATED       : Nov. 14, 1995
INVENTOR(S) : Paul E. Share

It is certified that error appears in the above-indentified patent and that said Letters Patent is hereby corrected as shown below:

In col. 3, line 43, delete [cycloalkenyl] and insert --cycloalkynyl--.

In col.10, Table 2, row 2, delete [55] and insert --5--.

Signed and Sealed this

Tenth Day of September, 1996

Attest:

BRUCE LEHMAN

Attesting Officer

Commissioner of Patents and Trademarks